United States Patent [19]

Cherpeck

[11] Patent Number: 5,484,463

[45] Date of Patent: Jan. 16, 1996

[54] POLY(OXYALKYLENE) HYDROXY AND AMINO AROMATIC CARBAMATES AND FUEL COMPOSITIONS CONTAINING THE SAME

[75] Inventor: Richard E. Cherpeck, Cotati, Calif.

[73] Assignee: Chevron Chemical Company, San Ramon, Calif.

[21] Appl. No.: 236,737

[22] Filed: May 2, 1994

[51] Int. Cl.⁶ .................................................. C10L 1/22
[52] U.S. Cl. .............................. 44/387; 560/24; 560/29; 560/32; 560/33; 560/20
[58] Field of Search .................................. 560/24, 29, 20, 560/32, 33; 44/387

[56] References Cited

U.S. PATENT DOCUMENTS

| | | | |
|---|---|---|---|
| 3,849,085 | 11/1974 | Kreuz et al. | 44/78 |
| 3,933,470 | 1/1976 | Cross et al. | 71/111 |
| 4,134,846 | 1/1979 | Machleder et al. | 252/51.5 A |
| 4,191,537 | 3/1980 | Lewis et al. | 44/71 |
| 4,320,021 | 3/1982 | Lange | 252/51.5 R |
| 4,347,148 | 3/1982 | Davis | 252/51.5 R |
| 4,357,351 | 11/1982 | Fancher et al. | 424/326 |
| 4,881,945 | 11/1989 | Buckley, III | 44/72 |
| 4,952,732 | 8/1990 | Speranza et al. | 564/390 |

OTHER PUBLICATIONS

Chemical Abstract Registry No. 85023-14-9 (no date).

Primary Examiner—Stephen Kalafut
Assistant Examiner—Cephia D. Toomer
Attorney, Agent, or Firm—C. J. Caroli

[57] ABSTRACT

Poly(oxyalkylene) hydroxy and amino aromatic carbamates having the formula:

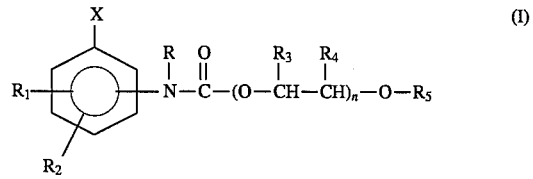

or a fuel-soluble salt thereof; wherein

X is hydroxy or amino;

R is hydrogen or lower alkyl having 1 to 6 carbon atoms;

$R_1$ and $R_2$ are each independently hydrogen, hydroxy, lower alkyl having 1 to 6 carbon atoms, lower alkoxy having 1 to 6 carbon atoms, nitro, amino, N-alkylamino wherein the alkyl group contains 1 to 6 carbon atoms, or N,N-dialkylamino wherein each alkyl group independently contains 1 to 6 carbon atoms;

$R_3$ and $R_4$ are each independently hydrogen or lower alkyl having 1 to 6 carbon atoms;

$R_5$ is hydrogen, alkyl having 1 to 30 carbon atoms, phenyl, aralkyl or alkaryl having 7 to 36 carbon atoms, or an acyl group having the formula:

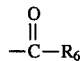

wherein $R_6$ is alkyl having 1 to 30 carbon atoms, phenyl, or aralkyl or alkaryl having 7 to 36 carbon atoms;

and n is an integer from 5 to 100.

The poly(oxyalkylene) hydroxy and amino aromatic carbamates of formula I are useful as fuel additives for the prevention and control of engine deposits.

33 Claims, No Drawings

POLY(OXYALKYLENE) HYDROXY AND AMINO AROMATIC CARBAMATES AND FUEL COMPOSITIONS CONTAINING THE SAME

BACKGROUND OF THE INVENTION

1. Field of the Invention

This invention relates to novel hydroxyaromatic compounds. More particularly, this invention relates to novel poly(oxyalkylene) hydroxy and amino aromatic carbamates and their use in fuel compositions to prevent and control engine deposits.

2. Description of the Related Art

It is well known that automobile engines tend to form deposits on the surface of engine components, such as carburetor ports, throttle bodies, fuel injectors, intake ports and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobilie's fuel consumption and production of exhaust pollutants. Therefore, the development of effective fuel detergents or "deposit control" additives to prevent or control such deposits is of considerable importance and numerous such materials are know in the art.

For example, aliphatic hydrocarbon-substituted phenols are known to reduce engine deposits when used in fuel compositions. U.S. Pat. No. 3,849,085, issued Nov. 19, 1974 to Kreuz et al., discloses a motor fuel composition comprising a mixture of hydrocarbons in the gasoline boiling range containing about 0.01 to 0.25 volume percent of a high molecular weight aliphatic hydrocarbon-substituted phenol in which the aliphatic hydrocarbon radical has an average molecular weight in the range of about 500 to 3,500. This patent teaches that gasoline compositions containing minor amount of an aliphatic hydrocarbon-substituted phenol not only prevent or inhibit the formation of intake valve and port deposits in a gasoline engine, but also enhance the performance of the fuel composition in engines designed to operate at higher operating temperatures with a minimum of decomposition and deposit formation in the manifold of the engine.

Similarly, U.S. Pat. No. 4,134,846, issued January 16, 1979 to Machleder et al., discloses a fuel additive composition comprising a mixture of (1) the reaction product of an aliphatic hydrocarbon-substituted phenol, epichlorohydrin and a primary or secondary mono- or polyamine, and (2) a polyalkylene phenol. This patent teaches that such compositions show excellent carburetor, induction system and combustion chamber detergency and, in addition, provide effective rust inhibition when used in hydrocarbon fuels at low concentrations.

Amino phenols are also known to function as detergents/dispersants, antioxidants and anti-corrosion agents when used in fuel compositions. U.S. Pat. No. 4,320,021, issued Mar. 16, 1982 to R. M. Lange, for example, discloses amino phenols having at least one substantially saturated hydrocarbon-based substituent of at least 30 carbon atoms. The amino phenols of this patent are taught to impart useful and desirable properties to oil-based lubricants and normally liquid fuels.

Nitro phenols have also been ,employed as fuel additives. For example, U.S. Pat. No. 4,347,148, issued Aug. 31, 1982 to K. E. Davis, discloses nitro phenols containing at least one aliphatic substituent having at least about 40 carbon atoms. The nitro phenols of this patent are taught to be useful as detergents, dispersants, antioxidants and demulsifiers for lubricating oil and fuel compositions.

Fuel additives containing a poly(oxyalkylene) moiety are also known in the art. For example, U.S. Pat. No. 4,191,537, issued Mar. 4, 1980 to R. A. Lewis et al., discloses a fuel composition comprising a major portion of hydrocarbons boiling in the gasoline range and from 30 to 2000 ppm of a hydrocarbyl poly(oxyalkylene) aminocarbamate having a molecular weight from about 600 to 10,000, and at least one basic nitrogen atom. The hydrocarbyl poly(oxyalkylene) moiety is composed of oxyalkylene units selected from 2 to 5 carbon oxyalkylene units. These fuel compositions are taught to maintain the cleanliness of intake systems without contributing to combustion chamber deposits.

Aromatic compounds containing a poly(oxyalkylene) moiety are also known in the art. For example, the above-mentioned U.S. Pat. No. 4,191,537, discloses alkylphenyl poly(oxyalkylene) polymers which are useful as intermediates in the preparation of alkylphenyl poly(oxyalkylene) aminocarbamates.

Similarly, U.S. Pat. No. 4,881,945, issued November 21, 1989 to Buckley, III, discloses alkylphenyl poly(oxyalkylene) aminocarbamates which are useful as fuel additives, wherein the alkyl group on the alkylphenyl moiety contains at least 40 carbon atoms.

Additionally, hydroxyaromatic compounds containing a poly(oxyalkylene) moiety are known in the art. For example, U S Pat. No. 4,952 732 issued August 28, 1990 to G. P. Speranza et al., discloses Mannich condensates prepared from a phenol, formaldehyde and an alkylamine containing propoxy groups and, optionally, ethoxy groups. These Mannich condensates are taught to be useful as corrosion inhibitors, water repellent agents, paint adhesion promotors, and also as intermediates for preparing surfactants, and polyols finding use in the manufacture of polyurethane foam.

U.S. Pat. No. 3,933,470, issued Jan. 20, 1976 to Cross et al., discloses esters of hydroxycarbanilic acid, wherein the ester moiety is straight or branched alkyl of 1 to carbon atoms, cycloalkyl, benzyl, chlorobenzyl, methylbenzyl, phenyl, chlorophenyl, methylphenyl, alkenyl of 2 to 6 carbon atoms, monohaloalkenyl, alkynyl of 2 to 6 carbon atoms, monohaloalkynyl, and monomethoxyalkynyl. This patent teaches such hydroxycarbanilic acid esters as intermediates in the preparation of alkynyloxy, alkenyloxy and cyanoalkoxy carbanilic acid esters, which are useful as herbicides for controlling broadleaf weeds and grasses.

It has now been discovered that certain hydroxy and amino aromatic carbamates having a poly(oxyalkylene) "tail" provide excellent control of engine deposits, especially intake valve deposits, when employed as fuel additives in fuel compositions.

SUMMARY OF THE INVENTION

The present invention provides novel poly(oxyalkylene) hydroxy and amino aromatic carbamates which are useful as fuel additives for the prevention and control of engine deposits, particularly intake valve deposits.

The poly(oxyalkylene) hydroxy and amino aromatic carbamates of the present invention have the formula:

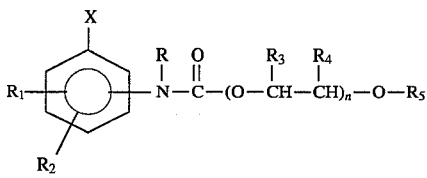

or a fuel-soluble salt thereof; wherein

X is hydroxy or amino;

R is hydrogen or lower alkyl having 1 to 6 carbon atoms;

$R_1$ and $R_2$ are each independently hydrogen, hydroxy, lower alkyl having 1 to 6 carbon atoms, lower alkoxy having 1 to 6 carbon atoms, nitro, amino, N-alkylamino wherein the alkyl group contains 1 to 6 carbon atoms, or N,N-dialkylamino wherein each alkyl group independently contains 1 to 6 carbon atoms;

$R_3$ and $R_4$ are each independently hydrogen or lower alkyl having 1 to 6 carbon atoms;

$R_5$ is hydrogen, alkyl having 1 to 30 carbon atoms, phenyl, aralkyl or alkaryl having 7 to 36 carbon atoms, or an acyl group having the formula:

wherein $R_6$ is alkyl having 1 to 30 carbon atoms, phenyl, or aralkyl or alkaryl having 7 to 36 carbon atoms;

and n is an integer from 5 to 100.

The present invention further provides a fuel composition comprising a major amount of hydrocarbon boiling in the gasoline or diesel range and an effective deposit-controlling amount of a poly(oxyalkylene) hydroxy or amino aromatic carbamate of the present invention.

The present invention additionally provides a fuel concentrate comprising an inert stable oleophilic organic solvent boiling in the range of from about 150° F. to 400° F. and from about 10 to 70 weight percent of a poly(oxyalkylene) hydroxy or amino aromatic carbamate of the present invention.

Among other factors, the present invention is based on the surprising discovery that certain poly(oxyalkylene) hydroxy and amino aromatic carbamates provide excellent control of engine deposits, especially on intake valves, when employed as fuel additives in fuel compositions.

DETAILED DESCRIPTION OF THE INVENTION

The fuel additives provided by the present invention have the general formula:

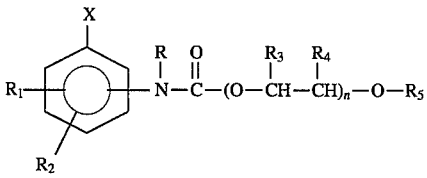

or a fuel-soluble salt thereof; wherein X, R, $R_1$, $R_2$, $R_3$, $R_4$, $R_5$, and n are as defined hereinabove.

In formula I above X can be hydroxy or amino. Preferably, X is hydroxy.

Preferably, R is hydrogen or lower alkyl of 1 to 4 carbon atoms. More preferably, R is hydrogen, methyl or ethyl.

Preferably, $R_1$ and $R_2$ are independently hydrogen, hydroxy, lower alkyl of 1 to 4 carbon atoms, nitro or amino. More preferably, $R_1$ and $R_2$ are independently hydrogen, hydroxy, nitro or amino. Most preferably, $R_1$ and $R_2$ are independently hydrogen, nitro or amino.

Preferably, one of $R_3$ and $R_4$ is lower alkyl having 1 to 3 carbon atoms and the other is hydrogen. More preferably, one of $R_3$ and $R_4$ is methyl or ethyl and the other is hydrogen. Most preferably, one of $R_3$ and $R_4$ is ethyl and the other is hydrogen.

$R_5$ is preferably hydrogen, alkyl having 2 to 24 carbon atoms, or alkylphenyl having an alkyl group containing 2 to 24 carbon atoms. More preferably, $R_5$ is hydrogen, alkyl having 4 to 12 carbon atoms or alkylphenyl having an alkyl group containing 4 to 12 carbon atoms. Most preferably, $R_5$ is alkylphenyl having an alkyl group containing 4 to 12 carbon atoms.

$R_6$ is preferably alkyl having 4 to 12 carbon atoms.

Preferably, n is an integer from 10 to 50. More preferably, n is an integer from 15 to 30.

When $R_1$ or $R_2$ is an N-alkylamino group, the alkyl group of the N-alkylamino moiety preferably contains 1 to 4 carbon atoms. More preferably, the alkyl group is methyl or ethyl. For example, particularly preferred N-alkylamino groups are N-methylamino and N-ethylamino groups.

Similarly, when $R_1$ or $R_2$ is an N,N-dialkylamino group, each alkyl group of the N,N-dialkylamino moiety preferably contains 1 to 4 carbon atoms. More preferably, each alkyl group is either methyl or ethyl. For example, particularly preferred N,N-dialkylamino groups are N,N-dimethylamino, N-ethyl-N-methylamino and N,N-diethylamino groups.

A preferred group of poly(oxyalkylene) aromatic carbamates are those of formula I wherein X is hydroxy; $R_1$ is hydrogen, hydroxy, lower alkyl of 1 to 4 carbon atoms, nitro or amino; $R_2$ is hydrogen, nitro or amino; and R is hydrogen.

A more preferred group of poly(oxyalkylene) aromatic carbamates are those of formula I wherein X is hydroxy; $R_1$ is hydrogen, hydroxy, nitro or amino; and $R_2$ and R are hydrogen. Even more preferably, $R_1$ is hydrogen, nitro or amino, and $R_2$ and R are hydrogen.

It is especially preferred that the aromatic hydroxyl or amino group present in the poly(oxyalkylene) hydroxyaromatic carbamates of this invention be situated in a meta or para position relative to the poly(oxyalkylene) carbamate moiety. When the aromatic moiety contains an additional hydroxy, nitro, amino, alkylamino or dialkylamino group, it is particularly preferred that the hydroxyl or amino group be in a meta or para position relative to the poly(oxyalkylene) carbamate moiety, and in an ortho position relative to the additional hydroxy, nitro, amino, alkylamino or dialkylamino group.

The poly(oxyalkylene) hydroxy and amino aromatic carbamates of the present invention will generally have a sufficient molecular weight so as to be non-volatile at normal engine intake valve operating temperatures (about 200°–250° C.). Typically, the molecular weight of the poly(oxyalkylene) hydroxy and amino aromatic carbamates of this invention will range from about 600 to about 10,000, preferably from 600 to 5,000, and more preferably from 1,000 to 3,000.

Generally, the poly(oxyalkylene) hydroxy and amino aromatic carbamates of this invention will contain an average of about 5 to about 100 oxyalkylene units; preferably, 10 to 50 oxyalkylene units; more preferably, 15 to 30 oxyalkylene units.

Fuel-soluble salts of the poly(oxyalkylene) hydroxy and amino aromatic carbamates of the present invention are also contemplated to be useful for preventing or controlling deposits. For those compounds containing a hydroxy group, such salts include alkali metal, alkaline earth metal, ammonium, substituted ammonium and sulfonium salts. Preferred metal salts are the alkali metal salts, particularly the sodium and potassium salts, and the substituted ammonium salts, particularly tetraalkyl-substituted ammonium salts, such as the tetrabutylammonium salts.

Fuel-soluble salts of the poly(oxyalkylene) aromatic carbamates of the present invention can also be readily prepared for those compounds containing an amino, N-alkylamino or N,N-dialkylamino group. Suitable salts include, for example, those obtained by protonating the amino moiety with a strong organic acid, such as an alkyl- or arylsulfonic acid. Preferred salts are derived from toluenesulfonic acid and methanesulfonic acid.

Definitions

As used herein, the following terms have the following meanings unless expressly stated to the contrary.

The term "amino" refers to the group: $-NH_2$.

The term "alkyl" refers to both straight- and branched-chain alkyl groups.

The term "lower alkyl" refers to alkyl groups having 1 to about 6 carbon atoms and includes primary, secondary and tertiary alkyl groups. Typical lower alkyl groups include, for example, methyl, ethyl, n-propyl, isopropyl, n-butyl, sec-butyl, t-butyl, n-pentyl, n-hexyl and the like.

The term "lower alkoxy" refers to the group $-OR_a$ wherein $R_a$ is lower alkyl. Typical lower alkoxy groups include methoxy, ethoxy, and the like.

The term "alkaryl" refers to the group:

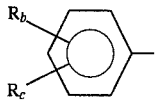

wherein $R_b$ and $R_c$ are each independently hydrogen or an alkyl group, with the proviso that both $R_b$ and $R_c$ are not hydrogen. Typical alkaryl groups include, for example, tolyl, xylyl, cumenyl, ethylphenyl, butylphenyl, dibutylphenyl, hexylphenyl, octylphenyl, dioctylphenyl, nonylphenyl, decylphenyl, didecylphenyl, dodecylphenyl, hexadecylphenyl, octadecylphenyl, icosylphenyl, tricontylphenyl and the like. The term "alkylphenyl" refers to an alkaryl group of the above formula in which $R_b$ is alkyl and $R_c$ is hydrogen.

The term "aralkyl" refers to the group:

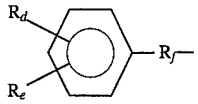

wherein $R_d$ and $R_e$ are each independently hydrogen or an alkyl group; and $R_f$ is an alkylene group. Typical alkaryl groups include, for example, benzyl, methylbenzyl, dimethylbenzyl, phenethyl, and the like.

The term "oxyalkylene unit" refers to an ether moiety having the general formula:

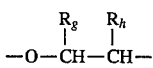

wherein $R_g$ and $R_h$ are each independently hydrogen or lower alkyl groups.

The term "poly(oxyalkylene)" refers to a polymer or oligomer having the general formula:

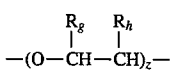

wherein $R_g$ and $R_h$ are as defined above, and z is an integer greater than 1. When referring herein to the number of poly(oxyalkylene) units in a particular poly(oxyalkylene) compound, it is to be understood that this number refers to the average number of poly(oxyalkylene) units in such compounds unless expressly stated to the contrary.

General Synthetic Procedures

The poly(oxyalkylene) hydroxy and amino aromatic carbamates of this invention may be prepared by the following general methods and procedures. It should be appreciated that where typical or preferred process conditions (e.g., reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

Moreover, those skilled in the art will recognize that it may be necessary to block or protect certain functional groups while conducting the following synthetic procedures. In such cases, the protecting group will serve to protect the functional group from undesired reactions or to block its undesired reaction with other functional groups or with the reagents used to carry out the desired chemical transformations. The proper choice of a protecting group for a particular functional group will be readily apparent to one skilled in the art. Various protecting groups and their introduction and removal are described, for example, in T. W. Greene and P. G. M. Wuts, *Protective Groups in Organic Synthesis*, Second Edition, Wiley, New York, 1991, and references cited therein.

In the present synthetic procedures, a hydroxyl group will preferably be protected, when necessary, as the benzyl or tert-butyldimethylsilyl ether. Introduction and removal of these protecting groups is well described in the art. Amino groups may also require protection and this may be accomplished by employing a standard amino protecting group, such as a benzyloxycarbonyl or a trifluoroacetyl group. Additionally, as will be discussed in further detail hereinbelow, the polyalkyl aromatic carbamates of this invention having an amino group on the aromatic moiety will generally be prepared from the corresponding nitro derivative. Accordingly, in many of the following procedures, a nitro group will serve as a protecting group for the amino moiety.

The poly(oxyalkylene) hydroxy and amino aromatic carbamates of the present invention having the formula:

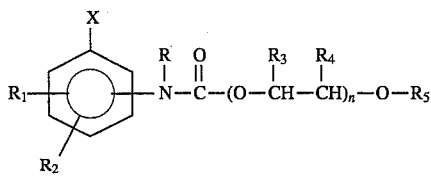 (III)

wherein X, R, $R_1$–$R_4$, and n are as defined above, and $R_5$ is an alkyl, phenyl, aralkyl or alkaryl group, may be prepared by reacting a poly(oxyalkylene) alcohol having the formula:

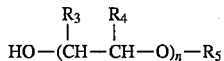 (IV)

wherein $R_3$, $R_4$, and n are as defined above, and $R_5$ is alkyl, phenyl, aralkyl or alkaryl, with phosgene, $COCl_2$, to provide a chloroformate ester having tile formula:

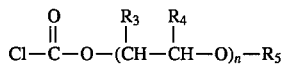 (V)

The above reaction may be represented as follows:

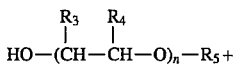
(IV)

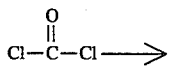

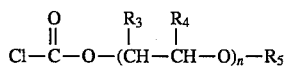
(V)

The resulting chloroformate ester of formula V is then reacted with a primary or secondary hydroxy or nitro aromatic amine havLng the formula:

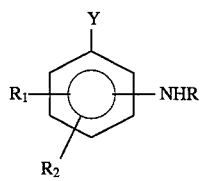 (VI)

wherein $R_1$, $R_2$ and R are as defined above, and Y is hydroxy or nitro, to provide the polyl[oxyalkylene) hydroxy or nitro aromatic carbamates of formula VII. This reaction may be represented as follows:

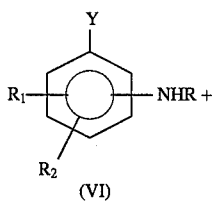
(VI)

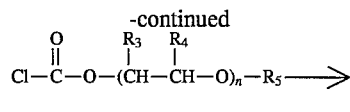
(V)

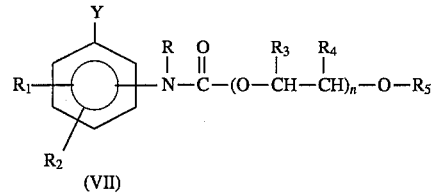
(VII)

For those compounds of formula VII where Y is a nitro group, reduction of the nitro group by conventional procedures will provide the desired poly(oxyalkylene) amino aromatic carbamates of formula III.

The hydroxy or nitro aromatic amines of formula VI are either known compounds or can be prepared from known compounds by conventional procedures. Suitable hydroxy or nitro aromatic amines for use as starting materials in this invention include 4-aminophenol, 2-nitro-4-aminophenol, 2-nitro-5-aminophenol, 2,6-dinitro-4-aminophenol, 4-(N-methylamino)phenol, 2-nitro-4-(N-methylamino)phenol, 2-nitro-5-(N-methylamino)phenol, 2,6-dinitro-4-(N-methylamino)phenol, 2-hydroxy-4-aminophenol, 2-hydroxy-4-(N-methylamino)phenol, 2,6-dihydroxy-4-aminophenol, 2,6-dihydroxy-4-(N-methylamino)phenol, 2-t-butyl-4-aminophenol, 2-t-butyl-4-(N-methylamino)phenol, 4-nitroaniline, 3-nitroaniline, 3, 4-dinitroaniline, and the like.

Preferred hydroxy or nitro aromatic amines of formula VI include 4-aminophenol, 2-nitro-4-aminophenol, 2-nitro-5-aminophenol, 2,6-di:nitro-4-aminophenol, 4-nitroaniline and 3-nitroaniline.

The poly(oxyalkylene) alcohols of formula IV may also be prepared by conventional procedures known in the art. Such procedures are taught, for example, in U.S. Pat. Nos. 2,782,240 and 2,841,479, which are incorporated herein by reference.

Preferably, the poly(oxyalkylene) alcohols of formula IV are prepared by contacting an alkoxide or phenoxide metal salt having the formula:

$R_5OM$ (VIII)

wherein $R_5$ is alkyl, phenyl, aralkyl or alkaryl, and M is a metal cation, such as lithium, sodium, or potassium, with about 5 to about 100 molar equivalents of an alkylene oxide (an epoxide) having the formula:

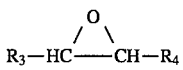 (IX)

wherein $R_3$ and $R_4$ are as defined above.

Generally, metal salt VIII is prepared by contacting the corresponding hydroxy compound $R_5OH$ with a strong base, such as sodium hydride, potassium hydride, sodium amide and the like, in an inert solvent, such as toluene, xylene and the like, under substantially anhydrous conditions at a temperature in the range from about −10° C. to about 120° C. for about 0.25 to about 3 hours.

Metal salt VIII is generally not isolated, but is reacted in situ with the alkylene oxide IX to provide, after neutralization, the poly(oxyalkylene) alcohol IV. This polymerization reaction is typically conducted in a substantially anhydrous inert solvent at a temperature of about 30° C. to about 150°

C. for about 2 to about 120 hours. Suitable solvents for this reaction, include toluene, xylene and the like. The reaction will generally be conducted at a pressure sufficient to contain the reactants and the solvent, preferably at atmospheric or ambient pressure.

The amount of alkylene oxide employed in this reaction will depend on the number of oxyalkylene units desired in the product. Typically, the molar ratio of alkylene oxide IX to metal salt VIII will range from about 5:1 to about 100:1; preferably, from 10:1 to 50:1, more preferably from 15:1 to 30:1.

Suitable alkylene oxides for use in the polymerization reaction include, for example, ethylene oxide; propylene oxide; butylene oxides, such as 1,2-butylene oxide (1,2-epoxybutane) and 2,3-butylene oxide (2,3-epoxybutane); pentylene oxides; hexylene oxides; octylene oxides and the like. Preferred alkylene oxides are propylene oxide and 1,2-butylene oxide.

In the polymerization reaction, a single type of alkylene oxide may be employed, e.g., propylene oxide, in which case the product is a homopolymer, e.g., a poly(oxypropylene). However, copolymer, are equally satisfactory and random copolymers are readily prepared by contacting the metal salt VIII with a mixture of alkylene oxides, such as a mixture of propylene oxide and 1,2-butylene oxide, under polymerization conditions. Copolymers containing blocks of oxyalkylene units are also suitable for use in the present invention. Block copolymers may be prepared by contacting the metal salt VII with first one alkylene oxide, then others in any order, or repetitively, under polymerization conditions.

The poly(oxyalkylene) alcohol IV may also be prepared by living or immortal polymerization as described by S. Inoue and T. Aida in *Encyclopedia of Polymer Science and Engineering*, Second Edition, Supplemental Volume, J. Wiley and Sons, New York, pages 412–420 (1989). These procedures are especially useful for preparing poly(oxyalkylene) alcohols of formula IV in which $R_3$ and $R_4$ are both alkyl groups.

As noted above, the alkoxide or phenoxide metal salt VIII is generally derived from the corresponding hydroxy compound, $R_5OH$. Preferred hydroxy compounds for use in this invention include straight- or branched-chain aliphatic alcohols having 1 to about 30 carbon atoms and phenols having the formula:

(X)

wherein $R_{13}$ and $R_{14}$ are each independently hydrogen or an alkyl group having 1 to about 30 carbon atoms.

Preferably, the straight- or branched-chain aliphatic alcohols employed in this invention will contain 2 to about 24 carbon atoms, more preferably 4 to 12 carbon atoms. Representative examples of straight- or branched-chain aliphatic alcohols suitable for use in this invention include, but are not limited to, n-butanol; isobutanol; sec-butanol; t-butanol; n-pentanol; n-hexanol; n-heptanol; n-octanol; isooctanol; n-nonanol; n-decanol; n-dodecanol; n-hexadecanol (cetyl alcohol); n-octadecanol (stearyl alcohol); alcohols derived from linear $C_{10}$ to $C_{30}$ alpha olefins and mixtures thereof; and alcohols derived from polymers of $C_2$ to $C_6$ olefins, such as alcohols derived from polypropylene and polybutene, including polypropylene alcohols having 9 to about 30 carbon atoms. Particularly preferred aliphatic alcohols are butanols.

The alkylphenols of formula X used in this invention may be monoalkyl-substituted phenols or dialkyl-substituted phenols. Monoalkyl-substituted phenols are preferred, especially monoalkylphenols having an alkyl substituent in the para position.

Preferably, the alkyl group of the alkylphenols employed in this invention will contain 2 to about 24 carbon atoms, more preferably 4 to 12 carbon atoms. Representative examples of phenols suitable for use in this invention include, phenol, methylphenol, dimethylphenol, ethylphenol, butylphenol, octylphenol, decylphenol, dodecylphenol, tetradecylphenol, hexadecylphenol, octadecylphenol, eicosylphenol, tetracosylphenol, hexacosylphenol, triacontylphenol and the like. Also, mixtures of alkylphenols may be employed, such as a mixture of $C_{14}$–$C_{18}$ alkylphenols, a mixture of $C_{18}$–$C_{24}$ alkylphenols, a mixture of $C_{20}$–$C_{24}$ alkylphenols, or a mixture of $C_{16}$–$C_{26}$ alkylphenols.

Particularly preferred alkylphenols are those derived from alkylation of phenol with polymers or oligomers of $C_3$ to $C_6$ olefins, such as polypropylene or polybutene. These polymers preferably contain 10 to 30 carbon atoms. An especially preferred alkylphenol is prepared by alkylating phenol with a propylene polymer having an average of 4 units, This polymer has the common name of propylene tetramer and is commercially available.

As indicated above, the poly(oxyalkylene) hydroxy and amino aromatic carbamates of formula III may be prepared by first reacting a poly(oxyalkylene) alcohol of formula IV with phosgene to form a chloroformate ester.

The reaction of the poly(oxyalkylene) alcohol of formula IV and phosgene is usually carried out on an essentially equimolar basis, although excess phosgene can be used to improve the degree of reaction. Any excess phosgene can be stripped from the chloroformate ester product prior to reaction with the hydroxy or nitro aromatic amine. The reaction is typically carried out at room temperature, although temperatures in the range of about –10° C. to 100° C., preferably about 0° C. to 50° C., may be employed. The reaction time will usually be in the range of about 0.5 to 48 hours. The reaction may be conducted in the presence or absence of an inert solvent, such as benzene, toluene, dichloromethane, and the like.

The resulting chloroformate ester of formula V is then reacted with a hydroxy or nitro aromatic amine of formula VI to form the poly(oxyalkylene) hydroxy or nitro aromatic carbamates of formula VII. Reduction of the nitro group provides the poly(oxyalkylene) amino aromatic carbamates of the invention.

The reaction of chloroformate ester with the hydroxy or nitro aromatic amine will generally be carried out in the presence of an aprotic solvent, such as methyl cyanide, DMF, acetone, chloroform, toluene or THF, containing a base acceptor, such as sodium bicarbonate, sodium carbonate, triethylamine or pyridine. The reaction will generally be carried out at room temperature, although higher or lower temperatures in the range of about –10° C. to 100° C. may be employed.

The mole ratio of the amine nitrogen to chloroformate ester will generally be in the range of about 1 to 10 moles of amine nitrogen per mole of chloroformate ester. The reaction time may vary from about 0.5 to about 48 hours. After reaction, the desired product may be isolated by conventional procedures, such as evaporation of the solvent, filtration and crystallization..

The poly(oxyalkylene) hydroxy or amino aromatic carbamates of the present invention wherein the group $R_5$ is hydrogen, that is, compounds having the formula:

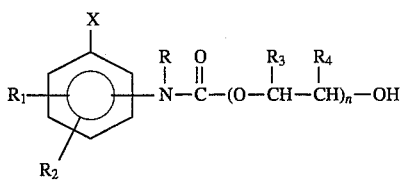

(XI)

wherein X, R, $R_1$–$R_4$, and n are as defined above, can be prepared from compounds of formula III, wherein $R_5$ is a benzyl group, by removing the benzyl group using conventional hydrogenolysis procedures. Compounds of formula III where $R_5$ represents a benzyl group may be prepared by employing a metal salt VIII derived from benzyl alcohol in the above-described synthetic procedures.

Similarly, the poly(oxyalkylene) hydroxy or amino aromatic carbamates of the present invention having the formula:

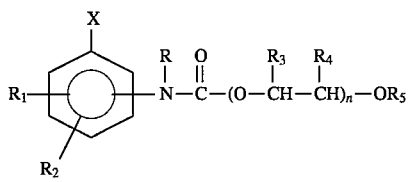

(XII)

wherein X, R, $R_1$–$R_4$, and n are as defined above, and $R_5$ is an acyl group having the formula:

wherein $R_6$ is as defined above, can be synthesized in several steps from a compound of formula III, wherein $R_5$ represents a benzyl group and the aromatic hydroxyl group or groups are protected by a hydroxyl protecting group that is stable to hydrogenolysis conditions, such as a tert-butyldimethyl-silyl group. The synthesis of carbamates of formula XII from such compounds may be effected by first removing the benzyl group using conventional hydrogenolysis conditions and then acylating the resulting hydroxyl group with a suitable acylating agent. Removal of the protecting group(s) from the aromatic hydroxyl group(s) using conventional procedures then provides a poly(oxyalkylene) hydroxy or amino aromatic carbamate of formula XII.

Suitable acylating agents for use in this reaction include acyl halides, such as acyl chlorides and bromides; and carboxylic acid anhydrides. Preferred acylating agents are those having the formula: $R_6C(O)$-Q, wherein $R_6$ is alkyl having 1 to 30 carbon atom, phenyl, or aralkyl or alkaryl having 7 to 36 carbon atoms, and Q is chloro or bromo.

A particularly preferred group of acylating agents are those having the formula: $R_6C(O)$-Q, wherein $R_6$ is alkyl having 4 to 12 carbon atoms. Representative examples of such acylating agents include acetyl chloride, propionyl chloride, butanoyl chloride, pivaloyl chloride, octanoyl chloride, decanoyl chloride and the like.

Generally, this acylation reaction will be conducted using about 0.95 to about 1.2 molar equivalents of the acylating agent. The reaction is typically conducted in an inert solvent, such as toluene, dichloromethane, diethyl ether and the like, at a temperature in the range of about 25° C. to about 150° C. for about 0.5 to about 48 hours. When an acyl halide is employed as the acylating agent, the reaction is preferably conducted in the presence of a sufficient amount of an amine capable of neutralizing the acid generated during the reaction, such as triethylamine, di(isopropyl)ethylamine, pyridine or 4-dimethylaminopyridine.

Although the poly(oxyalkylene) hydroxy and amino aromatic carbamates of the present invention may be conveniently prepared by the chloroformylation reaction described above, utilizing phosgene, it is also known in the art that other methods of producing carbamates are available using other reactants.

For example, the reaction of an isocyanate with an alcohol a also produces a carbamate. Accordingly, it is within the skill of the art to use a selected isocyanate-substituted nitro or protected hydroxyaromatic compound to react directly with a poly(oxyalkylene) alcohol to provide, after reduction of the nitro group, a carbamate within the scope of the present invention.

When necessary, protection of the aromatic hydroxyl groups on the hydroxyaromatic amines may be accomplished using well-known procedures. The choice of a suitable protecting group for a particular hydroxyaromatic amine will be apparent to those skilled in the art. Various protecting groups, and their introduction and removal, are described, for example, in To W. Greene and P. G. M. Wuts, *Protective Groups in Organic Synthesis*, Second Edition, Wiley, New York, 1991, and references cited therein.

Deprotection of the aromatic hydroxyl group(s) can also be accomplished using conventional procedures. Appropriate conditions for this deprotection step will depend upon the protecting group(s) utilized in the synthesis and will be readily apparent to those skilled in the art. For example, benzyl protecting groups may be removed by hydrogenolysis under 1 to about 4 atmospheres of hydrogen in the presence of a catalyst, such as palladium on carbon. Typically, this deprotection reaction is conducted in an inert solvent, preferably a mixture of ethyl acetate and acetic acid, at a temperature of from about 0° C. to about 40° C. for about 1 to about 24 hours.

When synthesizing the poly(oxyalkylene) aromatic carbamates of formula I having an amino group on the aromatic moiety (i.e., where X, $R_1$ and/or $R_2$ is an amino group), it is generally desirable to first prepare the corresponding nitro compound (i.e., wherein X, $R_1$ and/or $R_2$ is a nitro group) and then to reduce the nitro group to an amino group using conventional procedures. Aromatic nitro groups may be reduced to amino groups using a number of procedures that are well known in the art. For example, aromatic nitro groups may be reduced under catalytic hydrogenation conditions; or by using a reducing metal, such as zinc, tin, iron and the like, in the presence of an acid, such as dilute hydrochloric acid.

Generally, reduction of the nitro group by catalytic hydrogenation is preferred. Typically, this reaction is conducted using about 1 to 4 atmospheres of hydrogen and a platinum or palladium catalyst, such as palladium on carbon. The reaction is typically carried out at a temperature of about 0° C. to about 100° C. for about 1 to 24 hours in an inert solvent, such as ethanol, ethyl acetate and the like. Hydrogenation of aromatic nitro groups is discussed in further detail in, for example, P. N. Rylander, *Catalytic Hydrogenation in Organic Synthesis*, pp. 113–137, Academic Press (1979); and *Organic Synthesis, Collective Vol. 1*, Second Edition, pp. 240–241, John Wiley & Sons, Inc. (1941); and references cited therein.

Fuel Compositions

The poly(oxyalkylene) hydroxy and amino aromatic carbamates of the present invention are useful as additives in hydrocarbon fuels to prevent and control engine deposits, particularly intake valve deposits. The proper concentration of additive necessary to achieve the desired deposit control varies depending upon the type of fuel employed, the type of engine, and the presence of other fuel additives.

In general, the concentration of the poly(oxyalkylene) hydroxy and amino aromatic carbamates of this invention in hydrocarbon fuel will range from about 50 to about 2500 parts per million (ppm) by weight, preferably from 75 to 1,000 ppm. When other deposit control additives are present, a lesser amount of the present additive may be used.

The poly(oxyalkylene) hydroxy and amino aromatic carbamates of the present invention may be formulated as a concentrate using an inert stable oleophilic (i.e., dissolves in gasoline) organic solvent boiling in the range of about 150° F. to 400° F. (about 65° C. to 205° C.). Preferably, an aliphatic or an aromatic hydrocarbon solvent is used, such as benzene, toluene, xylene or higher-boiling aromatics or aromatic thinners. Aliphatic alcohols containing about 3 to 8 carbon atoms, such as isopropanol, isobutylcarbinol, n-butanol and the like, in combination with hydrocarbon solvents are also suitable for use with the present additives. In the concentrate, the amount of the additive will generally range from about 10 to about 70 weight percent, preferably 10 to 50 weight percent, more preferably from 20 to 40 weight percent.

In gasoline fuels, other fuel additives may be employed with the additives of the present invention, including, for example, oxygenates, such as t-butyl methyl ether, anti-knock agents, such as methylcyclopentadienyl manganese tricarbonyl, and other dispersants/detergents, such as hydrocarbyl amines, hydrocarbyl poly(oxyalkylene) amines, or succinimides. Additionally, antioxidants, metal deactivators and demulsifiers may be present.

In diesel fuels, other well-known additives can be employed, such as pour point depressants, flow improvers, cetane improvers, and the like.

A fuel-soluble, nonvolatile carrier fluid or oil may also be used with the poly(oxyalkylene) hydroxy and amino aromatic carbamates of this invention. The carrier fluid is a chemically inert hydrocarbon-soluble liquid vehicle which substantially increases the nonvolatile residue (NVR), or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, including hydrogenated and unhydrogenated polyalphaolefins, and synthetic polyoxyalkylene-derived oils, such as those described, for example, in U.S. Pat. No. 4, 191, 537 to Lewis, and polyesters, such as those described, for example, in U.S. Pat. Nos. 3, 756, 793 and 5,004,478 to Robinson and Vogel et al., respectively, and in European Patent Application Nos. 356, 726 and 382, 159, published Mar. 7, 1990 and Aug. 16, 1990, respectively.

These carrier fluids are believed to act as a carrier for the fuel additives of the present invention and to assist in removing and retarding deposits. The carrier fluid may also exhibit synergistic deposit control properties when used in combination with a poly(oxyalkylene) aromatic carbamate of this invention.

The carrier fluids are typically employed in amounts ranging from about 100 to about 5000 ppm by weight of the hydrocarbon fuel, preferably from 400 to 3000 ppm of the fuel. Preferably, the ratio of carrier fluid to deposit control additive will range from about 0.5:1 to about 10:1, more preferably from 1:1 to 4::1, most preferably about 2:1.

When employed in a fuel concentrate, carrier fluids will generally be present in amounts ranging from about 20 to about 60 weight percent, preferably from 30 to 50 weight percent.

EXAMPLE

The following examples are presented to illustrate specific embodiments of the present invention and synthetic preparations thereof; and should not be interpreted as limitations upon the scope of the invention.

Example 1

Preparation of α-(Chloroformyl)-ω-4-dodecylphenoxypolyoxybutylene)

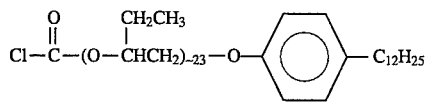

Toluene (300 mL) and phosgene (390 mL of a 20 weight percent solution in toluene) were cooled to 0° C. under nitrogen. α-Hydroxy-ω-4-dodecylphenoxypoly(oxybutylene) (255.7 grams) having an average of 23 oxybutylene units (prepared essentially as described in Example 6 of U.S. Pat. No. 4, 160, 648) was added dropwise. The cooling bath was removed and the reaction was stirred at room temperature for sixteen hours. The solvent was removed in vacuo to yield 258.0 grams of the desired chloroformate..

Example 2

Preparation of α(4-Hydroxy-3-nitrophenylcarbamoyl)-ω-4-dodecylphenoxypoly(oxybutylene)

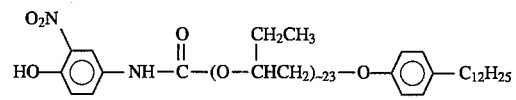

A solution of 176.8 grams of the product from Example 1 in chloroform (400 mL, filtered through activity 1 basic alumina) containing 9.24 grams of sodium bicarbonate and 15.4 grams of 4-amino-2-nitrophenol was refluxed for sixteen hours under nitrogen. The mixture was cooled to room temperature, diluted with dichloromethane (1.2 L) and washed once with saturated aqueous sodium bicarbonate solution, twice with water, and once with saturated aqueous sodium chloride. The organic layer was dried over anhydrous magnesium sulfate, filtered and concentrated in vacuo to yield 177 grams of an oil. The oil was chromatographed on silica gel eluting with hexane/diethyl ether/ethanol (70:25:5) to yield 159.3 grams of the desired product. The product had an average of 23 oxybutylene units. $^1$H NMR (CDCl$_3$) δ10.35 (s, 1H), 8.25 (bs, 1H), 7.3–7.9 (m, 2H), 7.05–7.3 (m, 3H), 6.7–6.9 (m, 2H), 4.8–5.0 (m, 1H), 3.85–4.05 (m, 2H), 3.1–3.85 (m, 66H), 0.5–1.8 (m, 140H).

Example 3

Preparation of
α-(4-Hydroxy-3-aminophenylcarbamoyl)-ω-4-
dodecylphenoxypoly(oxybutylene)

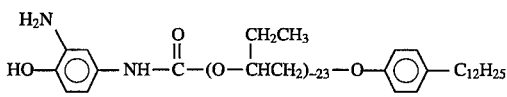

A solution of 35.0 grams of the product from Example 2 in 100 mL of ethylacetate containing 3.5 grams of 10% palladium on charcoal was hydrogenolyzed at 35–40 psi for sixteen hours on a Parr low-pressure hydrogenator. Catalyst filtration and removal of the solvent in vacuo yielded 32.0 grams of the desired product as a reddish-brown oil.

The product had an average of 23 oxybutylene units. $^1$H NMR (CDCl$_3$) δ7.15–7.25 (m, 2H), 6.6–7.0 (m, 4H), 6.5–6.6 (m, 1H), 4.8–4.95 (m, 1H), 3.9–4.1 (m, 2H), 3.1–3.9 (m, 66H), 0.5–1.8 (m, 140H).

Example 4

Preparation of α(4-Hydroxylphenylcarbamoyl)-ω4-
dodecylphenoxypoly(oxybutylene)

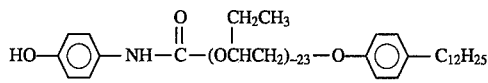

A solution of 22.5 grams of the product from Example 1 in chloroform (100 mL, filtered through activity 1 basic alumina) containing 1.2 grams of sodium bicarbonate and 1.4 grams of 4-aminophenol was refluxed for sixteen hours under nitrogen. The mixture was cooled to room temperature, diluted with dichloromethane (300 mL) and washed once with saturated aqueous sodium bicarbonate solution, twice with water, and once with saturated aqueous sodium chloride. The organic layer was dried over anhydrous magnesium sulfate, filtered, and concentrated in vacuo. The oil was chromatographed on silica gel eluting with hexane/diethyl ether (1:1) to yield 15.8 grams of the desired product. The product had an average of 23 oxybutylene units. IR (neat) 1728 cm$^{-1}$. $^1$H NMR (CDCl$_3$) δ6.95–7.25 (m, 4H), 6.6–7.25 (m, 4H), 4.75–4.9 (m, 1H), 3.85–4.0 (m, 2H), 3.1–3.85 (m, 66H), 0.5–1.8 (m, 140H).

Example 5

Preparation of
α(N-Methyl-4-Hydroxylphenylcarbamoyl)-ω-4-
dodecylphenoxypoly(oxybutylene)

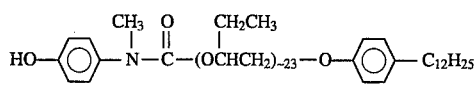

A solution of 4-N-methylaminophenol sulfate (6.89 grams) and triethylamine (9.2 mL) were stirred for 30 minutes in chloroform (100 mL, filtered through activity 1 basic alumina) at room temperature under nitrogen. 35.3 grams of the product from Example 1 were added and the reaction was refluxed for sixteen hours. The mixture was cooled to room temperature, diluted with dichloromethane (300 mL) and washed once with saturated aqueous sodium bicarbonate solution, twice with water, and once with saturated aqueous sodium chloride. The organic layer was dried over anhydrous magnesium sulfate, filtered and concentrated in vacuo. The oil was chromatographed on silica gel eluting with hexane/diethyl ether/ethanol (60:39:1) to yield 18.0 grams of the desired product. The product had an average of 23 oxybutylene units. IR (neat) 1709, 1682 cm$^{-1}$. $^1$H NMR (CDCl$_3$) δ7.15–7.6 (m, 3H), 7.0–7.15 (m, 2H), 6.7–6.9 (m, 4H), 4.75–4.95 (m, 1H), 3.95–4.1 (m, 2H), 3.1–3.85 (m, 69H), 0.5–1.8 (m, 140H).

Example 6

Single-Cylinder Engine Test

The test compounds were blended in gasoline and their deposit reducing capacity determined in an ASTM/CFR single-cylinder engine test.

A Waukesha CFR single-cylinder engine was used. Each run was carried out for 15 hours, at the end of which time the intake valve was removed, washed with hexane and weighed. The previously determined weight of the clean valve was subtracted from the weight of the value at the end of the run. The differences between the two weights is the weight of the deposit. A lesser amount of deposit indicates a superior additive. The operating conditions of the test were as follows: water jacket temperature 200° F.; vacuum of 12 in Hg, air-fuel ratio of 12, ignition spark timing of 40° BTC; engine speed is 1800 rpm; the crankcase oil is a commercial 30W oil.

The amount of carbonaceous deposit in milligrams on the intake valves is reported for each of the test compounds in Table I and Table II.

TABLE I

| Sample[1] | Intake Valve Deposit Weight (in milligrams) | | |
|---|---|---|---|
| | Run 1 | Run 2 | Average |
| Base Fuel | 253.4 | 235.5 | 244.5 |
| Example 2 | 30.1 | 23.2 | 26.7 |
| Example 3 | 9.9 | 7.2 | 8.6 |

[1]At 150 parts per million actives (ppma).

TABLE II

| Sample[1] | Intake Valve Deposit Weight (in milligrams) | | |
|---|---|---|---|
| | Run 1 | Run 2 | Average |
| Base Fuel | 302.6 | 300.4 | 301.5 |
| Example 4 | 5.7 | 4.5 | 5.1 |
| Example 5 | 53.0 | 52.0 | 52.5 |

[1]At 200 parts per million actives (ppma).

The base fuel employed in the above single-cylinder engine tests was a regular octane unleaded gasoline containing no fuel detergent. The test compounds were admixed with the base fuel to give concentrations of 150 and 200 ppma (parts per million actives), as indicated in the tables.

The data in Table I and Table II illustrates the significant reduction in intake valve deposits provided by the poly(oxyalkylene) aromatic carbamates of the present invention (Examples 2, 3, 4 and 5) compared to the base fuel.

What is claimed is:

1. A compound of the formula:

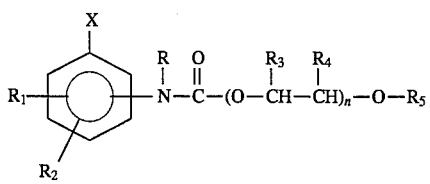

or a fuel-soluble salt thereof; wherein

X is hydroxy or amino;

R is hydrogen or lower alkyl having 1 to 6 carbon atoms;

$R_1$ and $R_2$ are each independently hydrogen, hydroxy, lower alkoxy having 1 to 6 carbon atoms, nitro, amino, N-alkylamino wherein the alkyl group contains 1 to 6 carbon atoms, or N,N-dialkylamino wherein each alkyl group independently contains 1 to 6 carbon atoms;

one of $R_3$ and $R_4$ is ethyl and the other is hydrogen;

$R_5$ is phenyl, aralkyl or alkaryl having 7 to 36 carbon atoms, or an acyl group having the formula:

wherein $R_6$ is alkyl having 1 to 30 carbon atoms, phenyl, or aralkyl or alkaryl having 7 to 36 carbon atoms;

and n is an integer from 10 to 50.

2. The compound according to claim 1, wherein n is an integer ranging from 15 to 30.

3. The compound according to claim 1, wherein $R_1$ and $R_2$ are independently hydrogen, hydroxy, lower alkyl of 1 to 4 carbon atoms, nitro or amino; and X is hydroxy.

4. The compound according to claim 3, wherein $R_1$ and $R_2$ are independently hydrogen, nitro or amino.

5. The compound according to claim 6, wherein $R_1$ is hydrogen, nitro or amino and $R_2$ is hydrogen.

6. The compound according to claim 1, wherein R is hydrogen or lower alkyl of 1 to 4 carbon atoms.

7. The compound according to claim 1, wherein $R_5$ is alkylphenyl having an alkyl group containing 2 to 24 carbon atoms.

8. The compound according to claim 7, wherein $R_5$ is alkylphenyl having an alkyl group containing 4 to 12 carbon atoms.

9. A fuel composition comprising a major amount of hydrocarbons boiling in the gasoline or diesel range and an effective detergent amount of a compound of the formula:

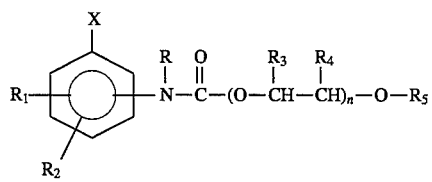

or a fuel-soluble salt thereof; wherein

X is hydroxy or amino;

R is hydrogen or lower alkyl having 1 to 6 carbon atoms;

$R_1$ and $R_2$ are each independently hydrogen, hydroxy, lower alkyl having 1 to 6 carbon atoms, lower alkoxy having 1 to 6 carbon atoms, nitro, amino, N-alkylamino wherein the alkyl group contains 1 to 6 carbon atoms, or N,N-dialkylamino wherein each alkyl group independently contains 1 to 6 carbon atoms;

$R_3$ and $R_4$ are each independently hydrogen or lower alkyl having 1 to 6 carbon atoms;

$R_5$ is hydrogen, alkyl having 1 to 30 carbon atoms, phenyl, aralkyl or alkaryl having 7 to 36 carbon atoms, or an acyl group having the formula:

wherein $R_6$ is alkyl having 1 to 30 carbon atoms, phenyl, or aralkyl or alkaryl having 7 to 36 carbon atoms;

and n is an integer from 5 to 100.

10. The fuel composition according to claim 9, wherein n is an integer ranging from 10 to 50.

11. The fuel composition according to claim 10, wherein n is an integer ranging from 15 to 30.

12. The fuel composition according to claim 9, wherein $R_1$ and $R_2$ are independently hydrogen, hydroxy, lower alkyl of 1 to 4 carbon atoms, nitro or amino; and X is hydroxy.

13. The fuel composition according to claim 12, wherein $R_1$ and $R_2$ are independently hydrogen, hydroxy, nitro or amino.

14. The fuel composition according to claim 13, wherein $R_1$ and $R_2$ are independently hydrogen, nitro or amino.

15. The fuel composition according to claim 14, wherein $R_1$ is hydrogen, nitro or amino and $R_2$ is hydrogen.

16. The fuel composition according to claim 9, wherein R is hydrogen or lower alkyl of 1 to 4 carbon atoms.

17. The fuel composition according to claim 9, wherein $R_5$ is hydrogen, alkyl having 2 to 24 carbon atoms, or alkylphenyl having an alkyl group containing 2 to 24 carbon atoms.

18. The fuel composition according to claim 17, wherein $R_5$ is hydrogen, alkyl having 4 to 12 carbon atoms, or alkylphenyl having an alkyl group containing 4 to 12 carbon atoms.

19. The fuel composition according to claim 9, wherein one of $R_3$ and $R_4$ is lower alkyl having 1 to 3 carbon atoms and the other is hydrogen.

20. The fuel composition according to claim 19, wherein one of $R_3$ and $R_4$ is methyl or ethyl and the other is hydrogen.

21. The fuel composition according to claim 9, wherein said composition contains about 50 to about 2500 parts per million by weight of said compound.

22. A fuel concentrate comprising an inert stable oleophilic organic solvent boiling in the range of from about 150° F. to 400° F. and from about 10 to about 70 weight percent of a compound of the formula:

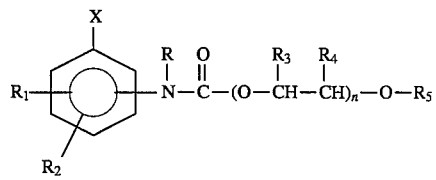

or a fuel-soluble salt thereof; wherein

X is hydroxy or amino;

R is hydrogen or lower alkyl having 1 to 6 carbon atoms;

$R_1$ and $R_2$ are each independently hydrogen, hydroxy, lower alkyl having 1 to 6 carbon atoms, lower alkoxy having 1 to 6 carbon atoms, nitro, amino, N-alkylamino wherein the alkyl group contains 1 to 6 carbon atoms, or N,N-dialkylamino wherein each alkyl group independently contains 1 to 6 carbon atoms;

$R_3$ and $R_4$ are each independently hydrogen or lower alkyl having 1 to 6 carbon atoms;

$R_5$ is hydrogen, alkyl having 1 to 30 carbon atoms, phenyl, aralkyl or alkaryl having 7 to 36 carbon atoms, or an acyl group having the formula:

wherein $R_6$ is alkyl having 1 to 30 carbon atoms, phenyl, or aralkyl or alkaryl having 7 to 36 carbon atoms;

and n is an integer from 5 to 100.

23. The fuel concentrate according to claim 24, wherein n is an integer ranging from 10 to 50.

24. The fuel concentrate according to claim 23, wherein n is an integer ranging from 15 to 30.

25. The fuel concentrate according to claim 24, wherein $R_1$ and $R_2$ are independently hydrogen, hydroxy, lower alkyl of 1 to 4 carbon atoms, nitro or amino; and X is hydroxy.

26. The fuel concentrate according to claim 25, wherein $R_1$ and $R_2$ are independently hydrogen, hydroxy, nitro or amino.

27. The fuel concentrate according to claim 26, wherein $R_1$ and $R_2$ are independently hydrogen, nitro or amino.

28. The fuel concentrate according to claim 27, wherein $R_1$ is hydrogen, nitro or amino and $R_2$ is hydrogen.

29. The fuel concentrate according to claim 22, wherein R is hydrogen or lower alkyl of 1 to 4 carbon atoms.

30. The fuel concentrate according to claim 22, wherein $R_5$ is hydrogen, alkyl having 2 to 24 carbon atoms, or alkylphenyl having an alkyl group containing 2 to 24 carbon atoms.

31. The fuel concentrate according to claim 30, wherein $R_5$ is hydrogen, alkyl having 4 to 12 carbon atoms, or alkylphenyl having an alkyl group containing 4 to 12 carbon atoms.

32. The fuel concentrate according to claim 22, wherein one of $R_3$ and $R_4$ is lower alkyl having 1 to 3 carbon atoms and the other is hydrogen.

33. The fuel concentrate according to claim 22, wherein one of $R_3$ and $R_4$ is methyl or ethyl and the other is hydrogen.

* * * * *